(12) United States Patent
Park et al.

(10) Patent No.: US 7,736,050 B2
(45) Date of Patent: Jun. 15, 2010

(54) FLUID MIXING DEVICE USING CROSS CHANNELS

(75) Inventors: Chin-sung Park, Yongin-si (KR); Joon-ho Kim, Seongnam-si (KR); Kak Namkoong, Seoul (KR); Kwang-wook Oh, Hwaseong-si (KR)

(73) Assignee: Samsung Electronics Co., Ltd. (KR)

( * ) Notice: Subject to any disclaimer, the term of this patent is extended or adjusted under 35 U.S.C. 154(b) by 907 days.

(21) Appl. No.: 11/433,594

(22) Filed: May 12, 2006

(65) Prior Publication Data

US 2006/0262642 A1    Nov. 23, 2006

(30) Foreign Application Priority Data

May 18, 2005    (KR)    ..................... 10-2005-0041765

(51) Int. Cl.
*B01F 5/00*    (2006.01)
(52) U.S. Cl. .................................... 366/162.1; 366/336
(58) Field of Classification Search ......... 366/336–341, 366/DIG. 1–DIG. 4, 162.1
See application file for complete search history.

(56) References Cited

U.S. PATENT DOCUMENTS

| | | | | |
|---|---|---|---|---|
| 1,319,572 | A * | 10/1919 | Di Sante | 96/331 |
| 4,516,632 | A * | 5/1985 | Swift et al. | 165/167 |
| 5,534,328 | A * | 7/1996 | Ashmead et al. | 428/166 |
| 5,869,004 | A | 2/1999 | Parce et al. | 422/100 |
| 6,299,657 | B1 * | 10/2001 | Schubert et al. | 48/197 FM |
| 6,305,834 | B1 * | 10/2001 | Schubert et al. | 366/144 |
| 2001/0042712 | A1 | 11/2001 | Battrell et al. | 210/511 |
| 2002/0187560 | A1 | 12/2002 | Pezzuto et al. | |
| 2004/0258571 | A1 * | 12/2004 | Lee et al. | 422/100 |
| 2004/0262223 | A1 * | 12/2004 | Strook et al. | 210/634 |
| 2005/0232076 | A1 * | 10/2005 | Yang et al. | 366/336 |

FOREIGN PATENT DOCUMENTS

JP    2001293345    10/2001

(Continued)

OTHER PUBLICATIONS

European Office Action; EP 06009691; Apr. 24, 2007.

(Continued)

*Primary Examiner*—David L Sorkin
(74) *Attorney, Agent, or Firm*—Cantor Colburn LLP (57) ABSTRACT

Provided is a fluid mixing device which produces a series of solutions with a concentration gradient. The fluid mixing device includes: a plurality of first channels disposed parallel to each other on a layer, and into which an equal amount of diluent flows from its upstream; a plurality of second channels formed perpendicular to the first channels on an adjacent layer to the layer on which the first channels are formed, and into which an equal amount of sample solution flows from its upstream; and via holes formed at at least one intersection between each of the first channel and a plurality of second channels so that a predetermined amount of sample solution flows from the second channels into corresponding first channels, wherein a series of solutions with different concentrations is produced in the first channels depending on the amount of sample solution that flows into the first channels through the via holes. Thus, a series of solutions with different concentrations is output from the first channels.

18 Claims, 8 Drawing Sheets

FOREIGN PATENT DOCUMENTS

| | | |
|---|---|---|
| KR | 1020030032811 A | 4/2003 |
| WO | WO03015890 | 2/2003 |

OTHER PUBLICATIONS

"Generating Fixed Concentration Arrays in a Microfluidic Device"; Authors: Matthew A. Holden, Saurabh Kumar, Edward T. Castellana, Ali Beskok, Paul S. Cremer; Sensors and Actuators B 92-2003. pp. 199-207.

"Microfluidic Devics for Electrokinetically Driven Parallel and Serial Mixing"; Authors: Stephen C. Jacobson, Timothy E. McKnight and J. Michael Ramsey; Anal. Chem. 1999, 71, pp. 4455-4459.

Japanese Office Action; Jul. 29, 2008. All references cited in the Japanese OA and not previously submitted are listed above.

* cited by examiner

FLUID MIXING DEVICE USING CROSS CHANNELS

BACKGROUND OF THE INVENTION

This application claims the priority of Korean Patent Application No. 10-2005-0041765, filed on May 18, 2005 in the Korean Intellectual Property Office, the disclosure of which is incorporated herein in its entirety by reference.

1. Field of the Invention

The present invention relates to a fluid mixing device for producing solutions with different concentrations of a sample solution and a diluent, and more particularly, to a fluid mixing device which produces a series of solutions with a concentration gradient with predetermined function from a plurality of channels by combining a sample solution and a diluent in a chip having a channel flow structure, without requiring a high electrical driving force.

2. Description of the Related Art

Generally, a fluid mixing device which produces a solution having a concentration gradient either produces an electrolyte solution having a various conductance (i.e., various concentration) used in an experiment for understanding dielectrophoretic properties of, for example, microparticles, or a series of sample solutions having concentration gradient such as a compound sample including a dye. In particular, producing a series of solutions with a concentration gradient by combining a sample solution and a diluent is called serial dilution, and a device which performs serial dilution in a chip is also known as a serial dilution chip.

An example of a conventional fluid mixing device which can be configured in a chip is a microfluidic device disclosed in "Microfluidic Devices for Electrokinetically Driven Parallel and Serial Mixing" (Anal. Chem., 1999, 71, 4455-4459). However, a high voltage in the range of 400 to 1,600 V is required for electrokinetic driving, and thus the microfluidic device cannot be applied to a portable lab on a chip. A microfluidic system disclosed in U.S. Pat. No. 5,869,004 uses electroosmosis, and thus additional devices and energy are required to apply a electric field to a microfluidic structure.

Other examples of conventional fluid mixing devices are microfluidic devices disclosed in "Generating Fixed Concentration Arrays in a Microfluidic Device" (Sensors and Actuators B 92,2003. 199-207) and U.S. Patent Publication No. 20010042712, which have a simple structure but take a long time to form a concentration gradient since it uses interdiffusion of laminar flows.

A microchannel apparatus for mixing liquids using a microchannel disclosed in Korean Patent Publication No. 2003-0032811 has a relatively simple structure but has a problem that the series of solutions by serial dilution have a linear concentration gradient. This is a problem because an exponential concentration gradient is required in many cases for serial dilution.

SUMMARY OF THE INVENTION

The present invention provides a fluid mixing device for producing a series of solutions with a concentration gradient by combining a sample solution and a diluent. The fluid mixing device does not require an additional electrical driving force and is configured in a chip so that it is can carried around with ease.

The present invention also provides a fluid mixing device which produces a series of solutions having an exponential concentration gradient when required.

According to an aspect of the present invention, there is provided a fluid mixing device which produces a series of solutions with different concentrations of a sample solution and a diluent. The fluid mixing device includes: a plurality of first channels disposed parallel to each other on a layer, and into which an equal amount of diluent flows from its upstream; a plurality of second channels formed perpendicular to the first channels on an adjacent layer to the layer on which the first channels are formed, and into which an equal amount of sample solution flows from its upstream; and via holes formed at at least one intersection between each of the first channel and a plurality of second channels so that a predetermined amount of sample solution flows from the second channels into corresponding first channels. A series of solutions with different concentrations is produced in the first channels depending on the amount of sample solution that flows into the first channels through the via holes.

The inside of the second channels may be maintained at a higher pressure than the inside of the first channels. The sample solution flows in from the first channels into the second channels due to the difference in pressure at both ends of the via holes. By making the number of via holes and areas of the via holes formed at the intersections of the first and second channels to be different, the amount of sample solution that is injected into the first channels can be different. As a result, various concentrations of the sample solution can be provided at the downstream of each of the first channels.

The inner pressure of the second channels may be maintained to be approximately the same, so that the amount of sample solution flowing into the first channels is proportional to the number of via holes and the area of the via holes. As a way to maintain the pressure inside all of the second channels to be the same, the same number of via holes may be formed in each of the second channels, and the total area of the via holes may be approximately the same.

According to another aspect of the present invention, there is provided a fluid mixing device which produces a series of solutions with different concentrations of a sample solution and a diluent. The fluid mixing device includes: a first plate having: a dilution channel unit having a plurality of first channels divided from a diluent injecting inlet disposed in an upper portion of the first plate; and a mixing channel unit having channels shaped in waves and extending downstream from the dilution channel unit; a second plate having: a sample solution channel unit disposed above the dilution channel unit, including: a plurality of second channels that are divided from a sample solution injecting inlet in an upper portion of the second plate and disposed perpendicular to the first channels; and via holes formed below the second channels at at least one intersection between each of the first channel and a plurality of second channels; and a cover in which apertures that respectively align with the diluent injecting inlet and the sample solution injecting inlet are formed, covering the top of the second plate.

The first plate may be made of a transparent material so optical characteristics of the solution at the downstream of the mixing channel unit can be observed. The cover can also be made of a transparent material so that the inside state of the sample solution channel unit when injecting the sample solution can be observed.

The second plate may be made of a material which can accurately and easily reflect the size of the area of the via holes determined according to the required concentration gradient. The second plate may be a silicon substrate when the sizes of the channels and the via holes are several to hundreds of micrometers, since the advanced semiconductor manufacturing technique can be used.

BRIEF DESCRIPTION OF THE DRAWINGS

The above and other features and advantages of the present invention will become more apparent by describing in detail exemplary embodiments thereof with reference to the attached drawings in which.

DETAILED DESCRIPTION OF THE INVENTION

The present invention will now be described more fully with reference to the accompanying drawings, in which exemplary embodiments of the invention are shown.

Figure 1:
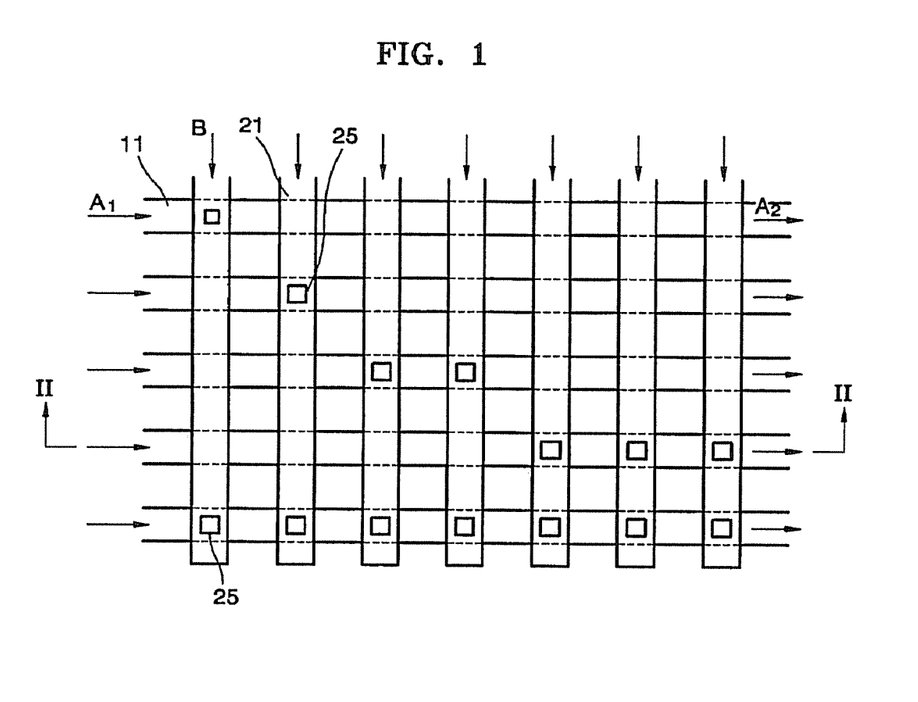
FIG. 1 is a schematic diagram illustrating a crossing channel structure according to an embodiment of the present invention.
Figure 2:
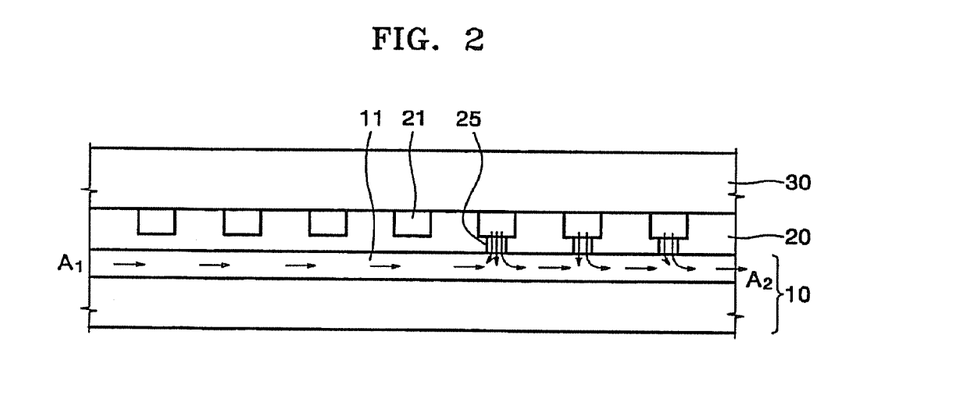
FIG. 2 is a cross-sectional view of the crossing channel structure illustrated in FIG. 1 taken along the line II-II.

FIG. 1 is a schematic diagram illustrating a crossing channel structure according to an embodiment of the present invention, and FIG. 2 is a cross-sectional view of the crossing channel structure illustrated in FIG. 1 taken along the line II-II. The principal of forming a series of solutions with a concentration gradient in the crossing channel structure according to the present embodiment will be described with reference to FIGS. 1 and 2. Referring to FIG. 1, first channels 11 are disposed horizontally and second channels 21 are disposed vertically on top of the first channels 11. Via holes 25 are selectively formed at the intersections of the first and second channels 11 and 21.

At least one via hole 25 is disposed in each of the first channels 11, and the number of via holes 25 in one of the first channels 11 can be different from the number of via holes 25 in the adjacent first channels 11. Even when the number of via holes 25 are the same for adjacent first channels 11, the total area of the via holes 25 are different, and thus different amount of sample solution flow into respective first channels 11. Also, the same number of via holes 25 are disposed in each of the second channels 21. For example, in FIG. 1, two via holes 25 are disposed in each of the second channels 21. In this case, the sample solution flows out through the same number of via holes 25 from the second channels 21, and thus, approximately the same pressure can be maintained in the second channels 21. More preferably, the total area of the two via holes 25 may be approximately the same so that the same pressure of the sample solution is maintained in the second channels 21.

The first channels 11 are formed parallel in a single layer. For example, in FIGS. 1 and 2, the first channels 11 are channel grooves formed as stripes in an upper portion of a first plate 10. The second channels 21 and the via holes 25 are formed in a second plate 20, above the first plate 10. The second channels 21 are formed perpendicular to the first channels 11 as striped channel grooves in an upper portion of the second plate 20, and the via holes 25 are selectively formed at the intersections of the first and second channels 11 and 21. The number and size of the via holes 25 are determined by the concentration of a solution required from each of the first channels 11. A cover 30 is formed on top of the second plate. The cover 30 may be composed of a transparent material.

The operation of the fluid mixing device is as follows. A diluent is injected into all the first channels 11 with the same flux at the upstream via the entrances of the first channels 11 in a direction indicted by arrows A1 while a sample solution is injected into all the second channels 21 in a direction indicated by arrows B. As illustrated in FIG. 2, the sample solution is diluted by the diluent as it flows into the first channels 11 through the via holes 25 and is output in a direction indicated by an arrow $A_2$. A structure in which the diluent and the sample solution are well mixed can be added at the downstream of the first channels 11 to produce a homogeneous solution.

Figure 3:
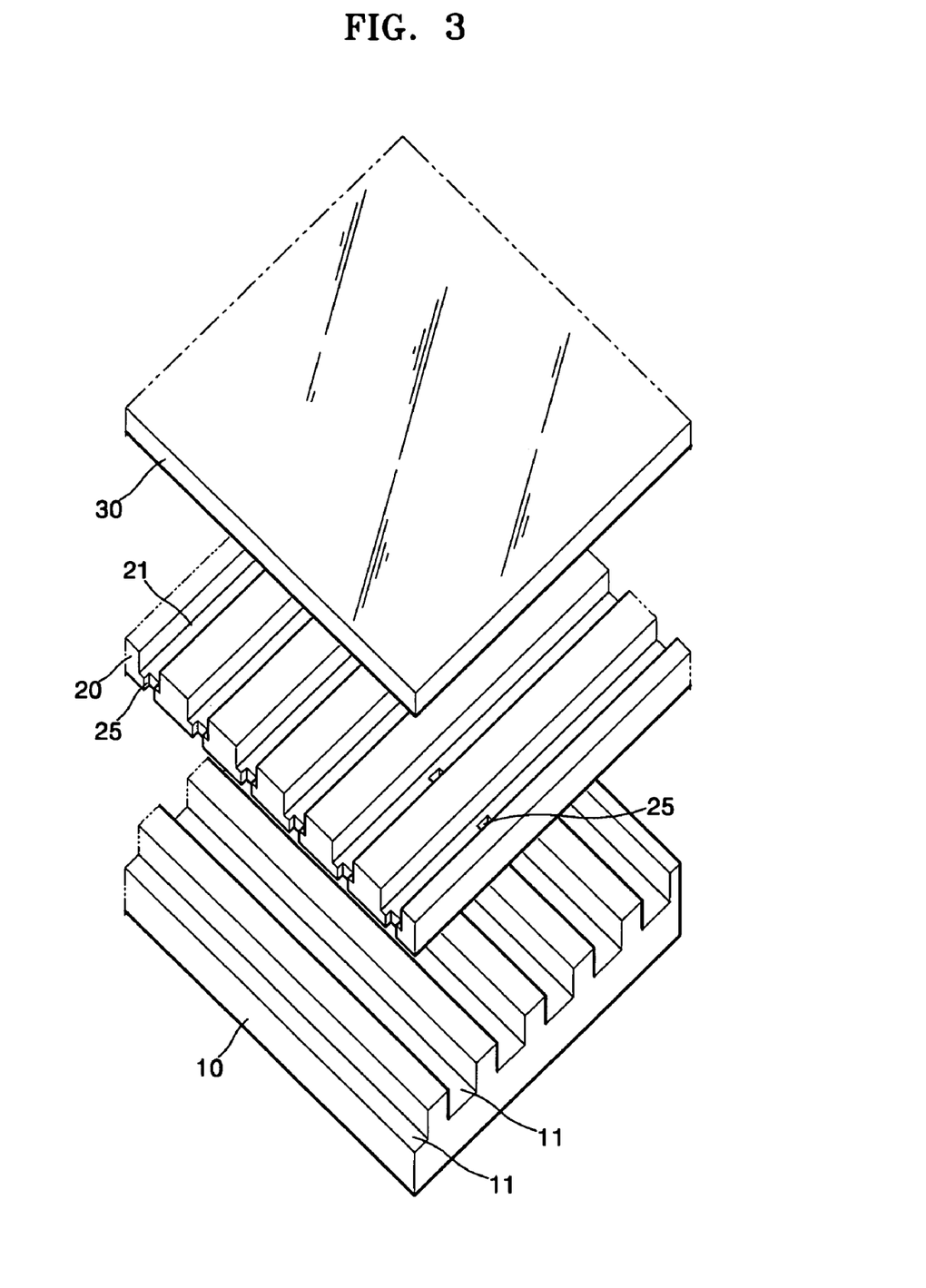
FIG. 3 is an exploded perspective view of the crossing channel structure illustrated in FIG. 1.

FIG. 3 is an exploded perspective view of the crossing channel structure illustrated in FIG. 1. As described above, the fluid mixing device using the crossing first and second channels 11 and 21 can be formed by stacking the first plate 10 in which the first channels 11 are formed, the second plate 20 in which the second channels 21 and the via holes 25 are formed, and the cover 30. However, such a three-layered structure is only one example, and the structure can be embodied in many ways. The structure is sufficient if first channels and second channels are formed crossing each other on different layers and via holes are selectively formed at the intersections of the first and second channels.

Figure 4:
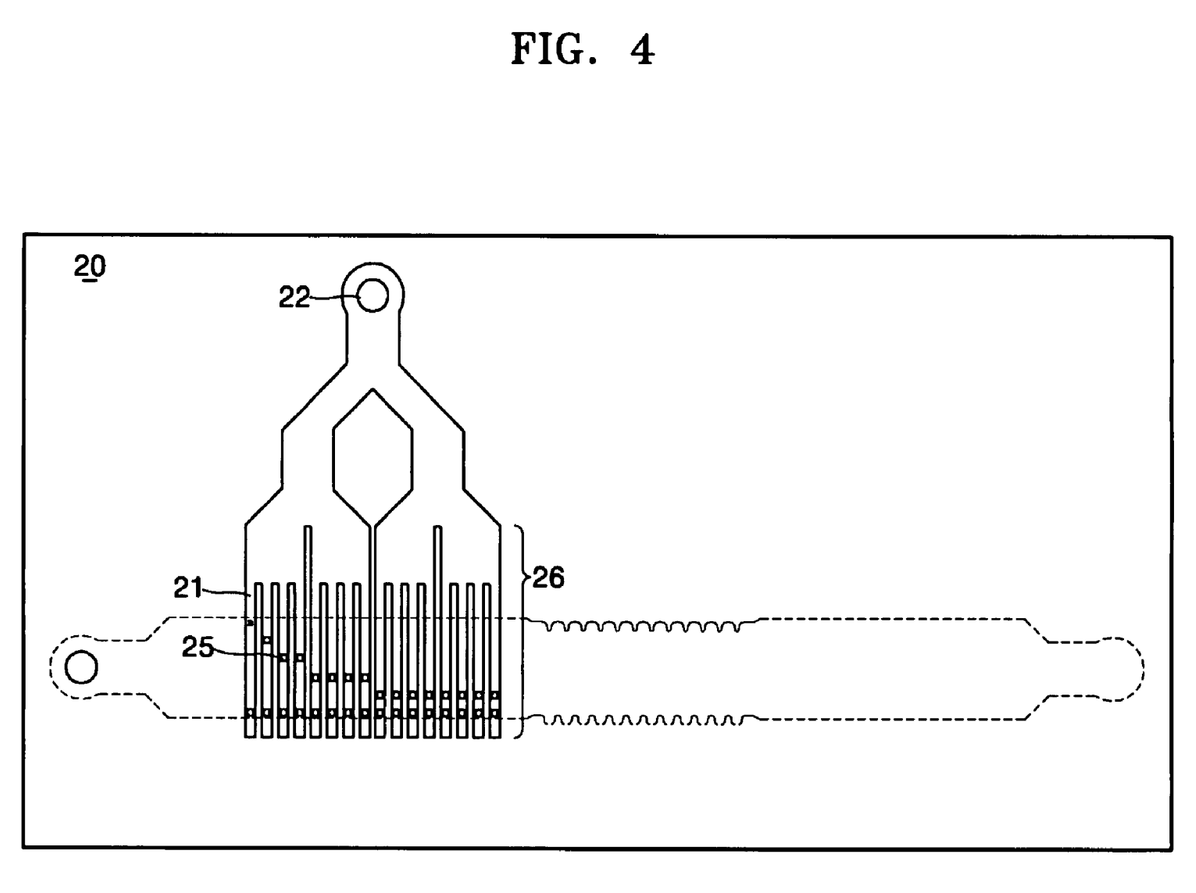
FIG. 4 is a plan view of a second plate illustrated in FIG. 2.

FIG. 4 is a plan view of the second plate 20 illustrated in FIG. 2. The fluid mixing device of the present embodiment includes the second plate 20 in which the second channels 21 and the via holes 25 are formed. A sample solution injecting inlet 22 is formed in a top surface of the second plate 20, and a sample solution channel unit 26 in which stripes of second channels 21 equally divided from the sample solution injecting inlet 22. Two via holes 25 are formed in each of the second channels 21 at a predetermined location. The predetermined locations are selected among the intersections between the second channels 21 and the first channels 11 disposed in a layer indicated by the dotted lines in FIG. 4, underneath the second plate 20. The second plate 20 may be a silicon substrate.

Figure 5:
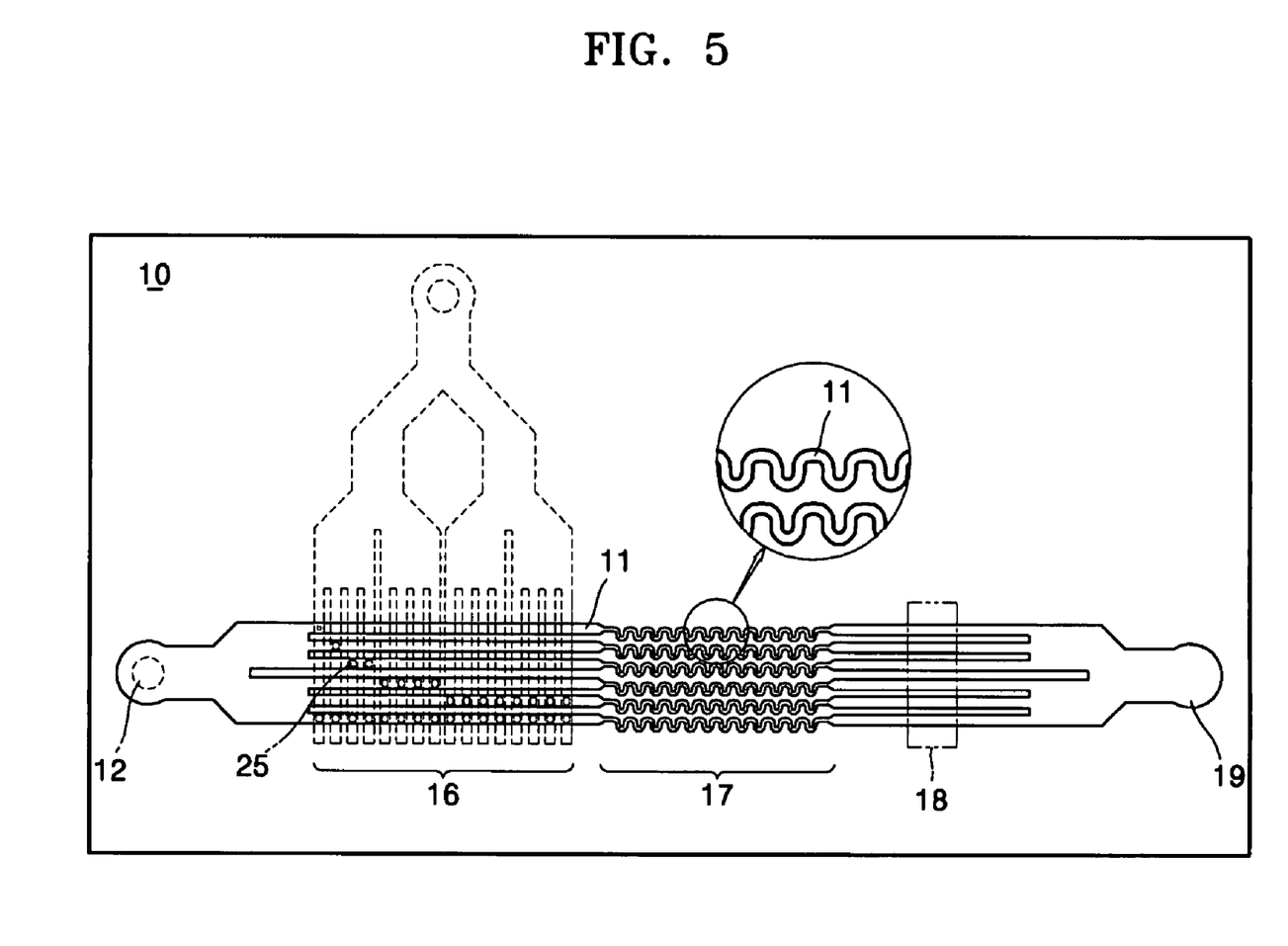
FIG. 5 is a plane view of a first plate illustrated in FIG. 2.

FIG. 5 is a plan view of the first plate 10 illustrated in FIG. 2. The fluid mixing device of the present embodiment includes the first plate 10 in which the first channels 11 are formed. A diluent injecting inlet 12 is formed in a top surface of the first plate 10, and a dilution channel unit 16 in which stripes of first channels 11 equally divided from the diluent injecting inlet 22. The dilution channel unit 16 is disposed perpendicular to the sample solution channel 26, downstream from the sample solution channel 26. The top surface of the first plate 10 and the bottom surface of the second plate 20 are connected to each other, and the via holes 25 selectively correspond to the intersections between the first and second channels 11 and 21 at the dilution channel unit 16.

A mixing channel unit 17 in which the first channels 11 are shaped like waves is formed downstream from the dilution channel unit 16. The solution produced by mixing the sample solution and the diluent at the dilution channel unit 16 becomes homogenous as it passes through the mixing channel unit 17. A homogeneous solution of the sample solution and the diluent are mixed in a predetermined concentration, in each of the first channels 11 is provided downstream from the mixing channel unit 17, and the output homogenous solution can be used for various purposes. If the fluid mixing device is to provide a sample for determining optical characteristics according to concentration, the fluid mixing device includes an observation deck 18 downstream from the mixing channel unit 17 as illustrated in FIG. 5 and an outlet 19 downstream from the observation unit 18.

The first plate 10 may be made of a transparent material so that optical characteristics of the solution can be observed. For example, the first plate 10 may be made of PDMS. PDMS is appropriate in many ways as the material for the first plate 10 since it is transparent, has excellent machining property, can be used to form channels on the order of μm relatively easily, and can be easily connected to a silicon substrate.

Although not illustrated in FIG. 5, the cover 30 is formed on top of the second plate 20. The cover 30 can be made of any material. The cover 30 may also be made of PDMS considering ease of manufacturing, but can also be a glass substrate or made of other plastic materials. Apertures corresponding to the sample solution injecting inlet 22, the diluent injecting inlet 12, and the outlet 19 are formed in the cover 30.

Below, the relationship between the number and size of via holes 25 required to obtain series of solutions with a desired concentration gradient using the fluid mixing device will be described.

When the total amount of influx of a sample solution entering an $n^{th}$ first channel among the first channels 11 is Xn times the flux of a diluent, the concentration Yn ($Y_n = X_n/(1+X_n)$) of the solution in the $n^{th}$ first channel can have a predetermined functional relationship with the natural number n if needed. That is, the fluid mixing device according to an embodiment of the present invention can produce a series of solutions with a concentration gradient having a predetermined function.

If required, Yn ($Y_n = y(n)$) can have an exponential relation to n. That is, the concentration of the solutions produced by the first channels 11 can be given by $Y_n = y(n) = y(n-1) \times 1/k$ (wherein n=2, 3, 4, . . . ), and in this case, it can be expressed as $Y_n = Y_1 \times (1/k)^{n-1}$.

In other words, Xn, that is, the amount of sample solution flowing into the first channels 11 from the second channels 21 of the sample solution channel unit 26 through the via holes 25, can be determined using $Y_n = X_n/(1+X_n)$ so that Yn has a predetermined exponential relation with n. The amount of total influx of the sample solution can be controlled by the number of via holes 25 and/or the size of the via holes 25 connected to each of the first channels 11.

For example, Table 1 illustrates the final concentration solution according to the number of via holes 25 corresponding to the first channels 11 and the length of one side of the via holes in the form of squares obtained using the above-mentioned equation when k=2.

TABLE 1

| Equation for Solution Concentration | Final Concentration of Solution | Volume of Sample Solution | No. of Via Holes | Volume of Sample Solution per 1 Via Hole | Size of Via Hole |
|---|---|---|---|---|---|
| $Y_1 = X_1/(1 + X_1)$ | 0.500 | 1.0000 | 20 | 51.15 | 7.15 |
| $Y_2 = X_2/(1 + X_2)$ | 0.250 | 0.3333 | 6 | 56.83 | 7.54 |
| $Y_3 = X_3/(1 + X_3)$ | 0.125 | 0.1429 | 4 | 36.54 | 6.04 |
| $Y_4 = X_4/(1 + X_4)$ | 0.063 | 0.0667 | 2 | 34.10 | 5.84 |
| $Y_5 = X_5/(1 + X_5)$ | 0.031 | 0.0323 | 1 | 33.00 | 5.74 |
| $Y_6 = X_6/(1 + X_6)$ | 0.016 | 0.0159 | 1 | 16.24 | 4.03 |

In order to produce a solution having a series of concentrations of $Y_n = Y_1 \times (1/2)^{n-1}$, the amount of the sample solution injected must be as shown in Table 1, and the appropriate number of via holes 25 is determined by the amount of sample solution to be injected. The area of each of the via holes 25 is determined to be proportional to the volume of the sample solution that is to be injected through the via holes 25.

The fluid mixing device using crossing channels of the present embodiment includes more number of second channels 21 than the maximum number of via holes 25 shown in Table 1, and the number of via holes 25 selectively formed in some of the intersections between the first and second channels 11 and 21 is indicated in Table 1. If the cross-sections of the via holes 25 are squares, the size of the via holes 25 in Table 1 indicate the length of one side of the square.

Figure 6A:
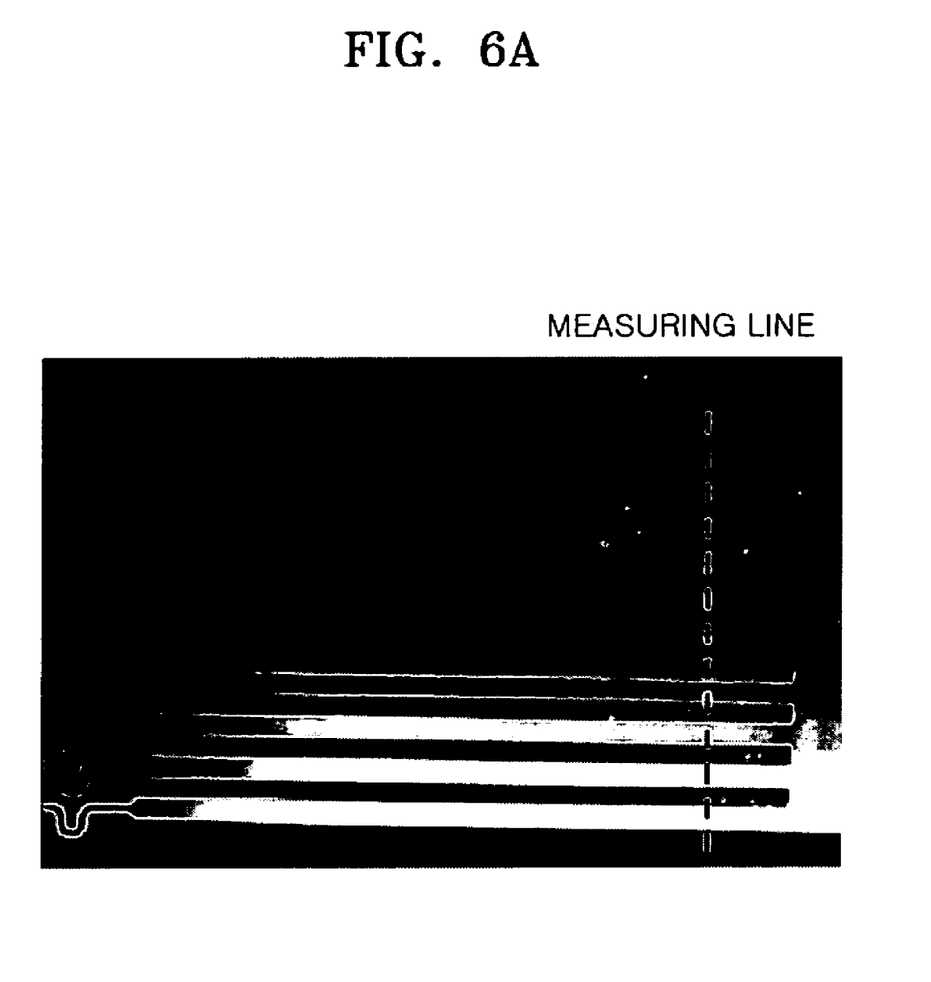
FIGS. 6A through 6C are views illustrating the results of a first experiment using the fluid mixing device illustrated in FIGS. 4 and 5.
Figure 6B:
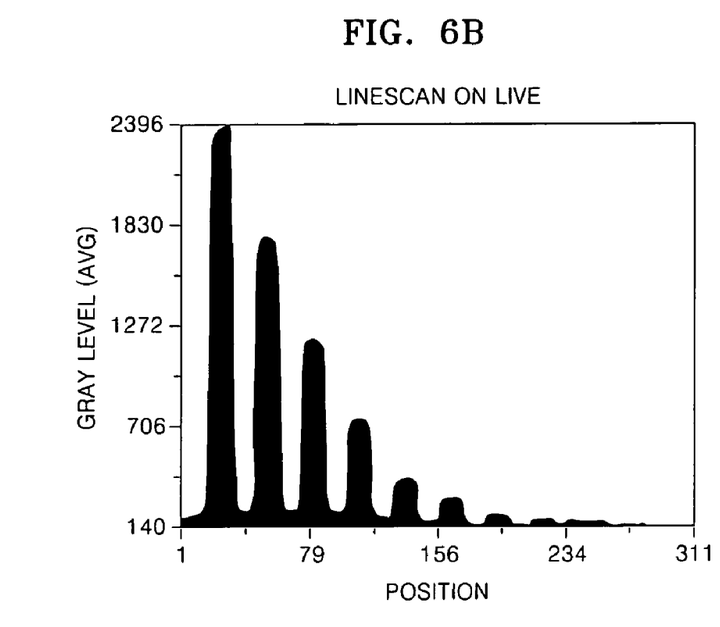
Figure 6C:
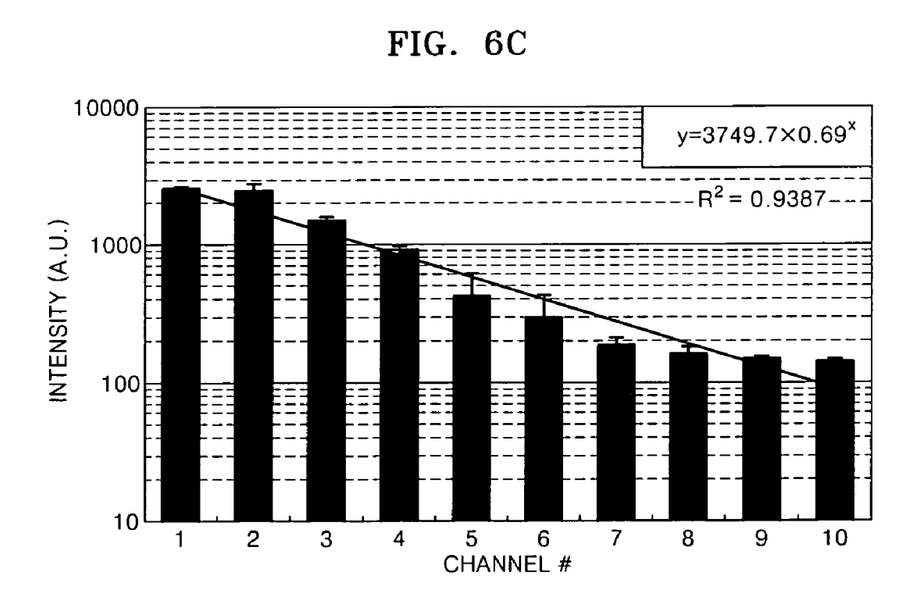

FIGS. 6A through 6C are views illustrating the results of a first experiment using the fluid mixing device illustrated in FIGS. 4 and 5 in which a PBS solution with a FITC concentration of 5 μM is injected at a rate of 300 μl/min. as a sample solution, and a PBS solvent is injected at a rate of 900 μl/min. as a diluent.

FIG. 6A is an image illustrating the visual effects a solution with various concentrations seen at the observation deck 18, FIG. 6B is a graph illustrating the brightness of the solution seen in FIG. 6A, and FIG. 6C is a semilog graph illustrating the brightness of the solution seen in FIG. 6A. The concentration gradient of the series of solutions produced from the fluid mixing device shows a linear line in the semilog graph illustrated in FIG. 6C. That is, the first and second channels 11 and 21 provide an exponential concentration gradient. The concentration of an $n^{th}$ first channel 11 is roughly $Y_n = 3749.7 \times 0.69^n$. Also, the first experiment shows that the fluid mixing device according to an embodiment of the present invention can produce a satisfactory concentration gradient for a relatively large amount of flux compared to conventional fluid mixing devices having microchannel fluidic structures.

Figure 7A:
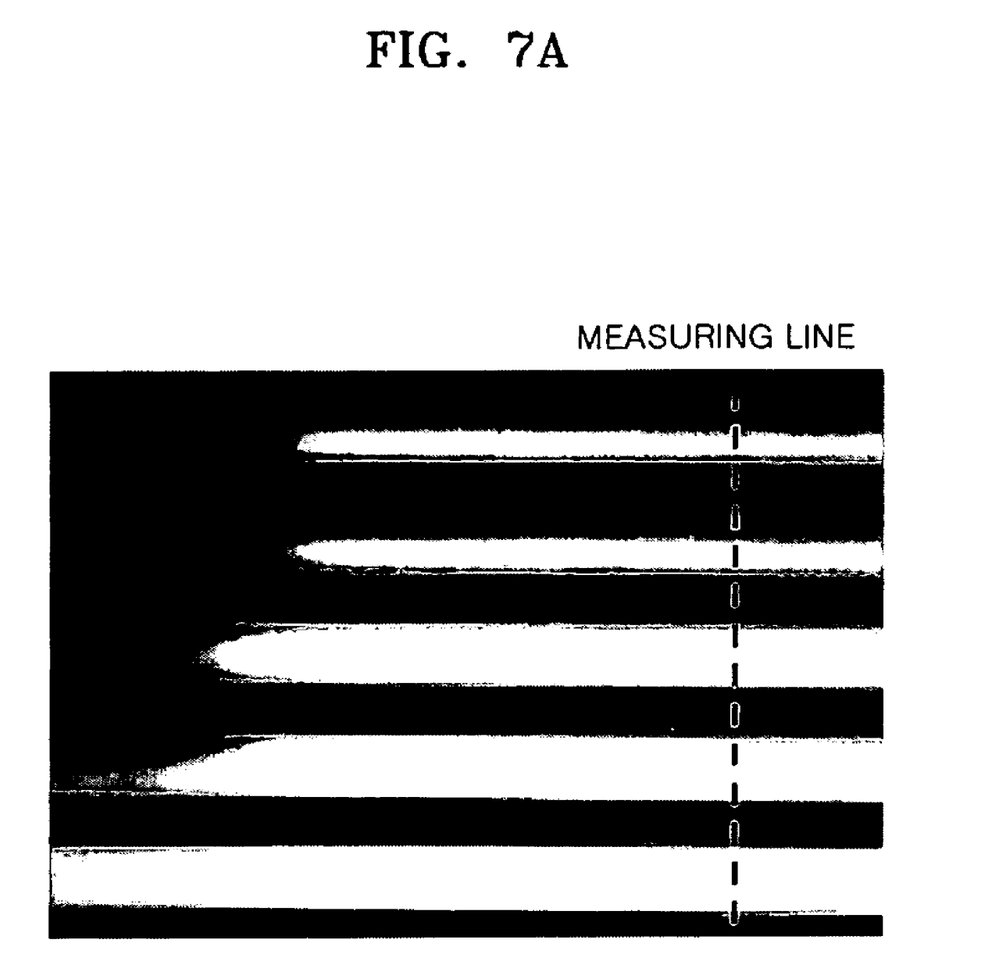
FIGS. 7A through 7C are views illustrating the results of a second experiment using the fluid mixing device illustrated in FIGS. 4 and 5.
Figure 7B:
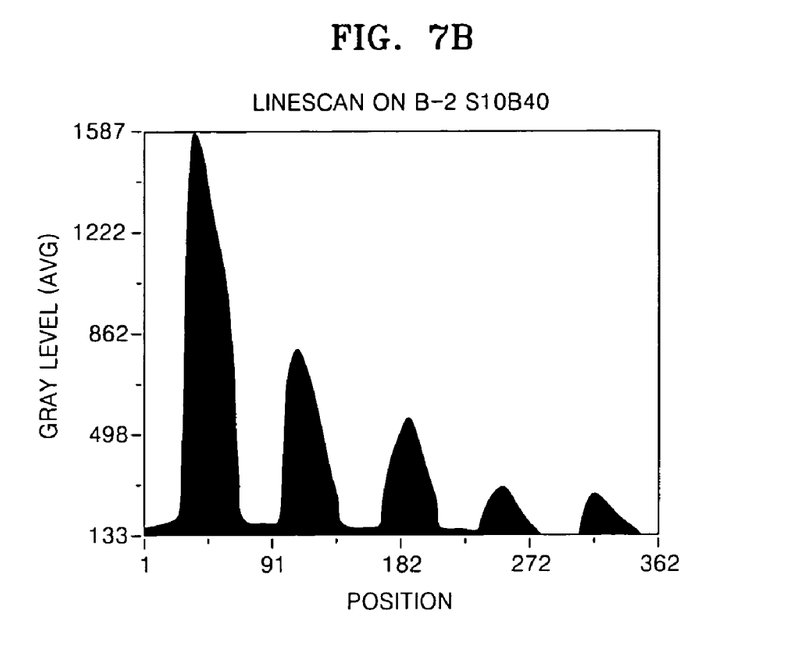
Figure 7C:
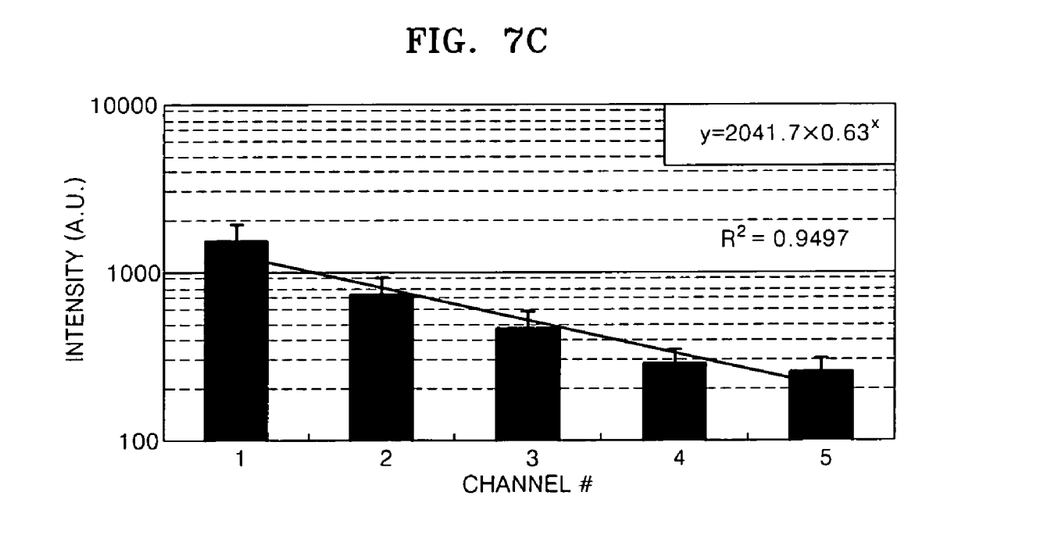

FIGS. 7A through 7C are views illustrating the results of a second experiment using the fluid mixing device illustrated in FIGS. 4 and 5 in which a PBS solution with a FITC concentration of 5 μM is injected at a rate of 10 μl/min. as a sample solution, and a PBS solvent is injected at a rate of 40 μl/min. as a diluent.

FIG. 7A is an image illustrating the visual effects of a solution with various concentrations seen at the observation deck 18, FIG. 7B is a graph illustrating the brightness of the solution seen in FIG. 7A, and FIG. 7C is a semilog graph illustrating the brightness of the solution seen in FIG. 7A. In the second experiment, the first and second channels 11 and 21 provide an exponential concentration gradient like in the first experiment. Furthermore, solutions with different concentrations can be produced by altering the fluxes of the sample solution and the diluent.

According to the above-described structure, the fluid mixing device of the present invention does not require a high electrical driving force and can be configured in a chip form, thereby being portable.

In addition, a series of solutions with an exponential concentration gradient can be easily obtained by changing the number and/or sizes of via holes if needed.

While the present invention has been particularly shown and described with reference to exemplary embodiments thereof, it will be understood by those of ordinary skill in the art that various changes in form and details may be made therein without departing from the spirit and scope of the present invention as defined by the following claims.

What is claimed is:

1. A fluid mixing device which produces a series of solutions with different concentrations of a sample solution and a diluent, the fluid mixing device comprising:

a plurality of first channels disposed parallel to each other on an upper portion of a layer, and into which an equal amount of diluent flows from its upstream, wherein the plurality of first channels are separated from each other;

a plurality of second channels formed perpendicular to the first channels on an upper portion of an adjacent layer to the layer on which the first channels are formed, and into which an equal amount of sample solution flows from its upstream, wherein the plurality of second channels are separated from each other; and via holes formed at at least one intersection between each of the first channel and a plurality of second channels so that a predetermined amount of sample solution flows from the second channels into corresponding first channels, wherein a number of via holes in one of the first channels is different from a number of via holes in adjacent first channels, or wherein the number of via holes in adjacent first channels is the same, and a total area of the via holes in one of the adjacent first channels is different than a total area of the via holes in another of the adjacent first channels, such that the series of solutions with different concentrations is produced in the first channels depending on the amount of sample solution that flows into the first channels through the via holes.

2. The fluid mixing device of claim 1, wherein the total area of the via holes connected to each of the first channels is proportional to the amount of sample solution that flows into the first channels.

3. The fluid mixing device of claim 1, wherein the pressure inside the second channels is approximately the same.

4. The fluid mixing device of claim 3, wherein the same number of via holes are formed in each of the second channels.

5. The fluid mixing device of claim 4, wherein the number of via holes in each of the second channels is 2.

6. The fluid mixing device of claim 3, wherein the total area of the via holes formed in each of the second channels is approximately the same.

7. The fluid mixing device of claim 1, wherein the first channels have a mixing part shaped in repeated waves downstream from the intersections with the second channels.

8. The fluid mixing device of claim 1, wherein, when the total influx of the sample solution into an $n^{th}$ first channel among the first channels is Xn times the flux of the diluent, the concentration $Y_n = X_n/(1+X_n)$ of the solution in the $n^{th}$ first channel has a predetermined functional relationship with a natural number n.

9. The fluid mixing device of claim 8, wherein the predetermined function is an exponential function.

10. The fluid mixing device of claim 1, wherein each of the via holes is directly connected to the first channel and the second channel at the intersection between the first and second channels.

11. A fluid mixing device which produces a series of solutions with different concentrations of a sample solution and a diluent, the fluid mixing device comprising:

a first plate including:
   a dilution channel unit having a plurality of first channels divided from a diluent injecting inlet disposed in an upper portion of the first plate; and
   a mixing channel unit having channels shaped in waves and extending downstream from the dilution channel unit;

a second plate including:
   a sample solution channel unit disposed above the dilution channel unit, having:
      a plurality of second channels that are divided from a sample solution injecting inlet in an upper portion of the second plate and disposed perpendicular to the first channels; and
      via holes formed below the second channels at at least one intersection between each of the first channel and a plurality of second channels; and a cover in which apertures that respectively align with the diluent injecting inlet and the sample solution injecting inlet are formed, covering the top of the second plate.

12. The fluid mixing device of claim 11 wherein the total area of the via holes connected to each of the first channels is formed to be proportional to the amount of sample solution that flows into the first channels.

13. The fluid mixing device of claim 11 wherein the pressure inside the second channels in the sample solution channel unit is approximately the same.

14. The fluid mixing device of claim 13 wherein the same number of via holes are formed in each of the second channels.

15. The fluid mixing device of claim 14 wherein the number of via holes in each of the second channels is 2.

16. The fluid mixing device of claim 13 wherein the total area of the via holes formed in each of the second channels is approximately the same.

17. The fluid mixing device of claim 11 wherein, when the total influx of the sample solution that flows into an $n^{th}$ first channel among the first channels is Xn times the flux of the diluent, the concentration $Y_n = X_n/(1+X_n)$ of the solution in the $n^{th}$ first channel has a predetermined functional relationship with a natural number n.

18. The fluid mixing device of claim 11, wherein the predetermined function is an exponential function.

* * * * *